(12) United States Patent
Gommé et al.

(10) Patent No.: US 12,239,434 B2
(45) Date of Patent: Mar. 4, 2025

(54) NEAR-FIELD POSITIONING DEVICE

(71) Applicant: NXP B.V., Eindhoven (NL)

(72) Inventors: Liesbeth Gommé, Anderlecht (BE); Anthony Kerselaers, Herselt (BE)

(73) Assignee: NXP B.V., Eindhoven (NL)

( * ) Notice: Subject to any disclaimer, the term of this patent is extended or adjusted under 35 U.S.C. 154(b) by 807 days.

(21) Appl. No.: 17/371,442

(22) Filed: Jul. 9, 2021

(65) Prior Publication Data

US 2023/0014117 A1    Jan. 19, 2023

(51) Int. Cl.
*A61B 5/107* (2006.01)
*G01S 11/06* (2006.01)

(52) U.S. Cl.
CPC .............. *A61B 5/107* (2013.01); *G01S 11/06* (2013.01)

(58) Field of Classification Search
CPC ................................. G01S 11/06; A61B 5/107
USPC ....................................................... 455/41.1
See application file for complete search history.

(56) References Cited

U.S. PATENT DOCUMENTS

| 9,692,526 | B2 | 6/2017 | Linnartz | |
|---|---|---|---|---|
| 9,819,075 | B2* | 11/2017 | Kerselaers | H04B 5/266 |
| 9,941,937 | B1* | 4/2018 | Kerselaers | H04B 5/26 |
| 10,014,960 | B1* | 7/2018 | Porat | H04W 4/023 |
| 10,108,984 | B2* | 10/2018 | Baldwin | H04L 63/0861 |
| 10,320,086 | B2* | 6/2019 | Kerselaers | H01Q 7/08 |
| 10,347,973 | B2* | 7/2019 | Kerselaers | H01Q 21/30 |
| 10,349,212 | B2 | 7/2019 | Tartz et al. | |
| 10,849,503 | B2* | 12/2020 | Melodia | A61B 5/0026 |
| 2018/0241482 | A1* | 8/2018 | Bostick | H04B 17/318 |
| 2018/0241483 | A1* | 8/2018 | Park | H04B 5/266 |
| 2019/0173519 | A1* | 6/2019 | Nabki | H04L 27/2647 |
| 2019/0296439 | A1* | 9/2019 | Kerselaers | H04B 5/26 |
| 2019/0363459 | A1* | 11/2019 | Geens | H01Q 1/273 |
| 2020/0106170 | A1* | 4/2020 | Kerselaers | H01Q 7/06 |

OTHER PUBLICATIONS

Yazdandoost et al.; "Channel Model for Body Area Network (BAN)"; IEEE P802.15 Working Group for Wireless Personal Area Networks (WPANs); Apr. 27, 2009; 61 pages.*
Frijis, Harold T.; "A Note on a Simple Transmission Formula"; IEEE Proceedings of the IRE, vol. 34, No. 5; 3 Pages (May 1946).
Communications: Principles and Practice—Ch. 3, pp. 102-104; Prentice Hall, New Jersey, USA; 6 pages (1996).

* cited by examiner

*Primary Examiner* — Mong-Thuy T Tran

(57) ABSTRACT

One example discloses a near-field positioning device, including: an input interface configured to receive a set of body-parameters from a user; a controller configured to generate a set of recommended positions for a set of near-field wireless devices to be coupled to the user based on the body-parameters; and an output interface configured to output the recommended positions.

17 Claims, 6 Drawing Sheets

| | EMPIRICAL FORMULA [dB] | | | |
|---|---|---|---|---|
| | $10\, a\, \log\left(\frac{1}{BP}\right) + b$ | | | |
| | a | b | BODY-PARAMETER | |
| LINK 1 | LEFT WRIST AND RIGHT LOWER LEG | 1.59 | -47.9 | WEIGHT [kg] |
| LINK 2 | LEFT WRIST AND LEFT UPPER ARM | 2.68 | -17 | WEIGHT [kg] |
| LINK 3 | LEFT ABDOMEN AND RIGHT ABDOMEN | 4.64 | 22.2 | FRONT BODY CIRCUMFERENCE [cm] |

FIG. 5

NEAR-FIELD POSITIONING DEVICE

The present specification relates to systems, methods, apparatuses, devices, articles of manufacture and instructions for a near-field positioning device.

SUMMARY

According to an example embodiment, a near-field positioning device, comprising: an input interface configured to receive a set of body-parameters from a user; a controller configured to generate a set of recommended positions for a set of near-field wireless devices to be coupled to the user based on the body-parameters; and an output interface configured to output the recommended positions.

In another example embodiment, the set of recommended positions is based on an on-body near-field channel loss model.

In another example embodiment, the near-field channel loss model is configured to predict a near-field channel loss over a range of user body-parameters.

In another example embodiment, the controller is configured to divide the set of near-field wireless devices into a set of device pairs, and define each device pair as a separate communications link; and a separate near-field channel loss model is calculated for each separate communications link based on the set of body-parameters.

In another example embodiment, the near-field channel loss model is configured to predict a near-field channel loss for the set of wireless devices located at a set of positions on the user.

In another example embodiment, the controller is configured to select the set of recommended positions from the set of positions having a near-field channel loss less than a maximum channel loss.

In another example embodiment, the controller is configured to rank the set of recommended positions from the set of positions from a lowest near-field to a highest near-field channel loss.

In another example embodiment, the controller is configured to receive from the input interface a fixed position for a first one of the set of near-field wireless devices; and the controller is configured to select a recommended position for a second one of the set of near-field wireless devices from the set of positions having a near-field channel loss less than a maximum channel loss.

In another example embodiment, the near-field channel loss model is $$\text{Near Field Link budget [dB]} = 10\ a\ \log\left(bp_0 \frac{1}{BP}\right) + b$$

wherein BP is a body-parameter from the set of body-parameters;
wherein $bp_0$ normalizes BP to a unitless quantity; and
wherein coefficients "a" and "b" are curve fitting coefficients.

In another example embodiment, "a" is a path loss exponent between a pair of devices in the set of near-field wireless devices.

In another example embodiment, the controller is configured to receive from the input interface an RSS (received signal strength) signal corresponding to a pair of wireless device positions; the controller is configured to transmit the RSS, the selected positions and the set of body-parameters from the output interface to a near-field channel loss model training site; and the training site is configured to add the RSS, the selected positions and the set of body-parameters to a set of training data used to update the near-field channel loss model.

In another example embodiment, the body-parameters include at least one of a body: topology, weight, height, girth, or position.

In another example embodiment, the controller is configured to substitute a mean body-parameter if a corresponding body-parameter is not received from the user.

In another example embodiment, the mean body-parameter is an average value of the corresponding body-parameter based on a set of training data collected from a set of users.

In another example embodiment, the near-field positioning device is embedded in a near-field wireless device from the set of near-field wireless devices; the near-field wireless device includes a front-end portion configured to translate signals from the controller into near-field signals exchanged with a second near-field device; and the front-end portion includes, a near-field antenna having a first conductive surface and a second conductive surface; wherein the conductive surfaces are configured to carry non-propagating quasi-static near-field electric-induction (NFEI) signals exchanged within the near-field communications link; and a tuning circuit coupled to the near-field antenna and having a set of tuning parameters and configured to adjust a resonant frequency and bandwidth of the near-field antenna.

In another example embodiment, the near-field positioning device is embedded in a near-field wireless device from the set of near-field wireless devices; the near-field wireless device includes a front-end portion configured to translate signals from the controller into near-field signals exchanged with a second near-field device; and the front-end portion includes, a near-field antenna having a coil; wherein the coil is configured to carry non-propagating quasi-static near-field magnetic-induction (NFMI) signals exchanged within the near-field communications link; and a tuning circuit coupled to the near-field antenna and having a set of tuning parameters and configured to adjust a resonant frequency and bandwidth of the near-field antenna.

In another example embodiment, the user is at least one of: a robot, a vehicle, a docking system, a physical coupling system, a ticketing station, a security portal, an assembly line device, a human body, an animal body, a body of a living organism, or a body structure of an inanimate object.

In another example embodiment, the near-field device is embedded in at least one of: a vehicle, a game controller, an amusement park ride, a medical device, an industrial station, or a robotic device.

According to an example embodiment, a method of enabling near-field positioning device to be operated, comprising: distributing a set of instructions, stored on a non-transitory, tangible computer readable storage medium, for configuring the near-field positioning device; wherein the instructions include: receiving a set of body-parameters from a user; generating a set of recommended positions for a set of near-field wireless devices to be coupled to the user based on the body-parameters; and outputting the recommended positions to the user.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings.

BRIEF DESCRIPTION OF THE DRAWINGS

FIG. 5 shows an example table of near-field channel loss model constants created for Links (1, 2, 3).

Figure 1:
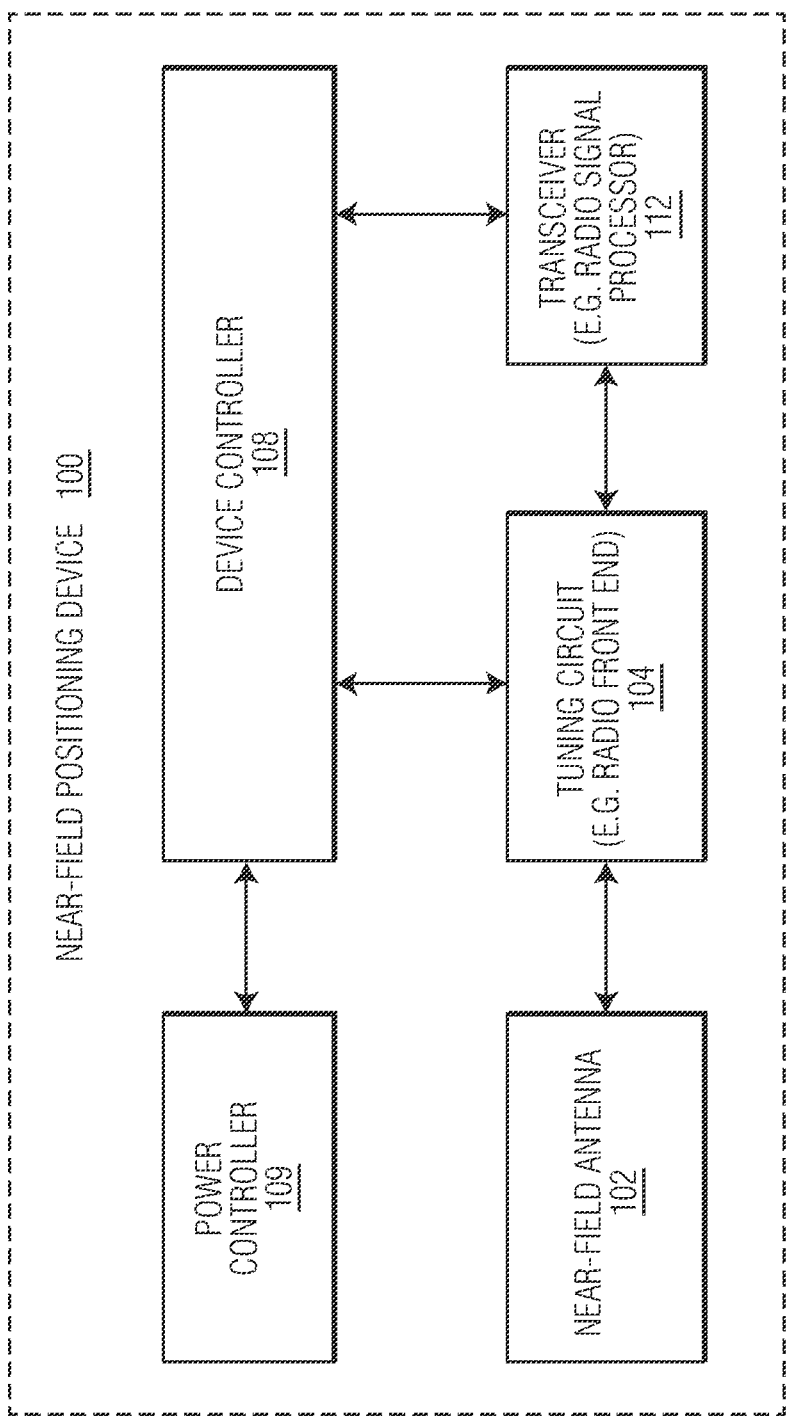
FIG. 1 is an example of a near-field device.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Wireless devices communications are known for a flexibility they provide to users in a variety of environments. Wireless devices using near-field communications are particularly useful when a limited communication range is desired/required since they do not create much far field energy that can disturb other systems or be undesirably detected. Such near-field devices are well suited for communication near a human body since such near-fields couple to the body.

However, all wireless communications can experience link drop-outs, attenuation, fading, shadowing etc. resulting in not only missed data transfers, but also possibly putting their medical users at risk.

Ensuring robust on-body near-field communication can become a trial and error process for users. Near-field devices are positioned by the user at a limited set of locations as specified by the manufacturer and RSS (received signal strength) measurements are taken. Drop-outs or communication link failures associated with a particular set of positions may be noted and then another set of positions specified by the manufacturer are tried out. This approach is not only laborious but also may not be possible for some wholly or partially incapacitated users. Such signal loss may not be acceptable, particularly in a medical context.

Now discussed is a near-field positioning device for a set of near-field wireless devices that generates a recommended set of near-field device positions based on various user body-parameters such as: body topology (e.g. shape, weight, height, girth, etc.), body positioning, and off-body environmental factors, which may or may not vary in response to user movements.

The near-field positioning device is configured to input a set of user body-parameters and using a calculated near-field channel loss (i.e. attenuation) model, identify one or more inter-device near-field positions which will result in an acceptable inter-device near-field channel loss taking varying inter-device orientations into account.

The near-field interactions between one or more near-field devices discussed herein can involve either on-body and/or off-body near-field devices. On-body devices are those near-field devices on a user's body or the body of a conductive surface. Off-body devices are defined with reference to the on-body devices and include any other near-field device that is not on-body as defined earlier. While the near-field channel model is an on-body model, there can also be near-field interactions between on-body devices and other off-body devices.

These near-field devices can be based on either near-field electromagnetic induction (NFEMI), where the transmitter and receiver are coupled by both magnetic (H) and electric (E) fields, near-field electric-induction (NFEI), where the transmitter and receiver are coupled by electric (E) fields, and near-field magnetic-induction (NFMI/NFC), where the transmitter and receiver are coupled by magnetic (H) fields. While RF wireless communication is accomplished by propagating an RF plane wave through free space, NFEMI, NFEI, NFMI and NFC communicates using non-propagating quasi-static E and/or H field signals.

In various example embodiments, a first near-field antenna includes a near-field electric-induction antenna (e.g. such as either a NFEI or NFEMI antenna) and is configured for on-body communications. A second near-field antenna includes a near-field magnetic-induction antenna (e.g. such as an NFC antenna) and is configured for off-body communications.

For example, an on-body sensor in a first near-field wireless device can be configured to communicate the sensor's readings to a second on-body near-field wireless device that collects the sensor's readings and perhaps other user information as well. A third off-body wireless device could be a smartphone/NFC reader that energizes the second on-body near-field wireless device that collected the sensor's readings, and thereby prompts the second on-body near-field wireless device to transmit the collected the sensor's readings to the smartphone/NFC reader.

Note, while example embodiments discussed herein refer to a user's body, on-body and off-body, body is herein broadly defined to include at least: a human's body, an animal's body, a body of a living organism, a body structure of an inanimate object, a robot, a vehicle, a docking system, a physical coupling system, a station on an assembly line, and so on.

In a near-field device, an H-field antenna (i.e. magnetic antenna) is primarily sensitive to magnetic fields and/or primarily initiates magnetic fields when driven by a current. Any E-field component from an H-field antenna is strongly reduced (e.g. −20 to −60 dB reduction, a factor of 0.1 to 0.0008 (10% to 0.08%) depending on the antenna design).

A small loop antenna is an example H-field antenna and includes a loop antenna with dimensions much smaller than the wavelength of its use. The small loop antenna does not resonate at the NFEMI carrier frequency but is instead tuned to resonance by an external reactance. In some example embodiments the current in the small loop antenna has in every position of the loop the same value.

Also in a near-field device, an E-field antenna (i.e. electric antenna) is primarily sensitive to electric fields and/or primarily initiates electric fields when driven by a voltage. Any H-field component from an E-field antenna is strongly reduced (e.g. −20 to −60 dB reduction, a factor of 0.1 to 0.0008 (10% to 0.08%) depending on the antenna design).

A short loaded dipole antenna is an example E-field antenna and includes a short dipole with dimensions much smaller than the NFEMI carrier frequency and in some example embodiments has extra capacitance surfaces at both ends.

The quasi-static characteristic of these fields is a result of the NFEMI antenna dimensions in combination with their carrier frequencies. Most of the near-field energy is stored in the form of magnetic and electric fields, while a small amount of RF energy inevitably propagates in free space. Small antenna geometries minimize radiating waves in free space.

FIG. 1 is an example of a near-field wireless positioning device 100. The example near-field wireless positioning device 100 includes a near-field antenna 102, a tuning circuit 104 (e.g. radio front end), a device controller 108, power controller 109, and a transceiver circuit 112 (e.g. radio signal processor). An example of the near-field antenna 102 is presented and discussed in FIG. 2.

The tuning circuit 104 is configured to adjust the positioning device's 100 resonance frequency using a capacitive bank (C-bank), and bandwidth using a resistive bank (R-bank) in response to signals from the transceiver circuit 112 and the device controller 108. The C-bank and R-bank discretes are in some examples about 130 pF and 5000 ohms respectively to support the required resonance frequency (e.g. 10.6 MHz) and bandwidth (e.g. 400 KHz). The device controller 108 is configured to adjust (e.g. increment/decrement) the C-bank and R-bank values using the tuning circuit 104.

The device controller 108 is configured to monitor and maintain the positioning device's 100 operational resonance frequency and operational bandwidth/quality factor of the near-field signals (e.g. NFEI or NFEMI) carried by the near-field antenna. The device controller 108 is configured to adjust tuning parameters in the tuning circuit 104 if either the operational resonance frequency is different from a preselected resonance frequency and/or the operational bandwidth is different from a preselected bandwidth.

The device controller 108 is also configured to monitor one or more near-field communications link characteristics (e.g. RSS (Received Signal Strength). While the near-field communications link characteristic of RSS is discussed herein, RSS is only one example of a near-field communications link characteristic. Other near-field communications link characteristics include: a tuning parameter of the tuning circuit 104, data throughput in the near-field communications link, or a number of lost data packets in the near-field communications link.

In some example embodiments, the controller 108 is configured to receive a set of body-parameters from a user. The controller 108 configured to generate a set of recommended positions for a set of near-field wireless devices to be coupled to the user based on the body-parameters and output the recommended positions to the user.

The set of recommended positions are based on a near-field channel loss model. The near-field channel loss model is configured to predict a near-field channel loss over a range of user body-parameters.

In some example embodiments the controller 108 is configured to divide the set of near-field wireless devices into a set of device pairs, and define each device pair as a separate communications link. The controller 108 then calculates a separate near-field channel loss model for each separate communications link based on the set of body-parameters. The near-field channel loss model is configured to predict a near-field channel loss for the set of wireless devices located at a set of positions on the user.

The controller 108 then selects the set of recommended positions from the set of positions having a near-field channel loss less than a maximum channel loss. In some example embodiments the controller 108 ranks the set of recommended positions from the set of positions from a lowest near-field to a highest near-field channel loss (e.g. a strongest predicted SNR to a weakest predicted SNR).

In some example embodiments, the maximum channel loss may be set so that the margin to receive sensitivity at each node belonging to a pair of wireless devices is at least 20 dB to account for possible severe external/ambient random interference, such that only those positions are selected having a near-field channel loss less than this maximum channel loss.

In some example embodiments the controller 108 receives from the input interface a fixed position for a first one of the set of near-field wireless devices. The controller 108 then selects a recommended position for a second one of the set of near-field wireless devices from the set of positions having a near-field channel loss less than a maximum channel loss.

In some example embodiments the controller 108 is configured to receive from the input interface an RSS (received signal strength) signal corresponding to a pair of wireless device positions. The controller 108 then transmits the RSS, the selected positions and the set of body-parameters from the output interface to a near-field channel loss model training site (e.g. back to the manufacture of the near-field positioning device 100) where the training site is configured to add the RSS, the selected positions and the set of body-parameters to a set of training data used to update the near-field channel loss model.

The body-parameters can include at least one of a body: topology, weight, height, girth, or position. In some example embodiments the controller 108 is configured to substitute a mean body-parameter if a corresponding body-parameter is not received from the user. The mean body-parameter is an average value of the corresponding body-parameter based on a set of training data collected from a set of users.

In some example embodiments the near-field positioning device 100 is embedded in one or more of the near-field wireless device from the set of near-field wireless devices. In other example embodiments the near-field positioning device 100 is remote and communicates the set of recommended positions to the set of near-field wireless devices.

In various example embodiments the user can be: a robot, a vehicle, a docking system, a physical coupling system, a ticketing station, a security portal, an assembly line device, a human body, an animal body, a body of a living organism, or a body structure of an inanimate object.

In various example embodiments the near-field positioning device 100 is embedded in at least one of: a vehicle, a game controller, an amusement park ride, a medical device, an industrial station, or a robotic device.

Figure 2:
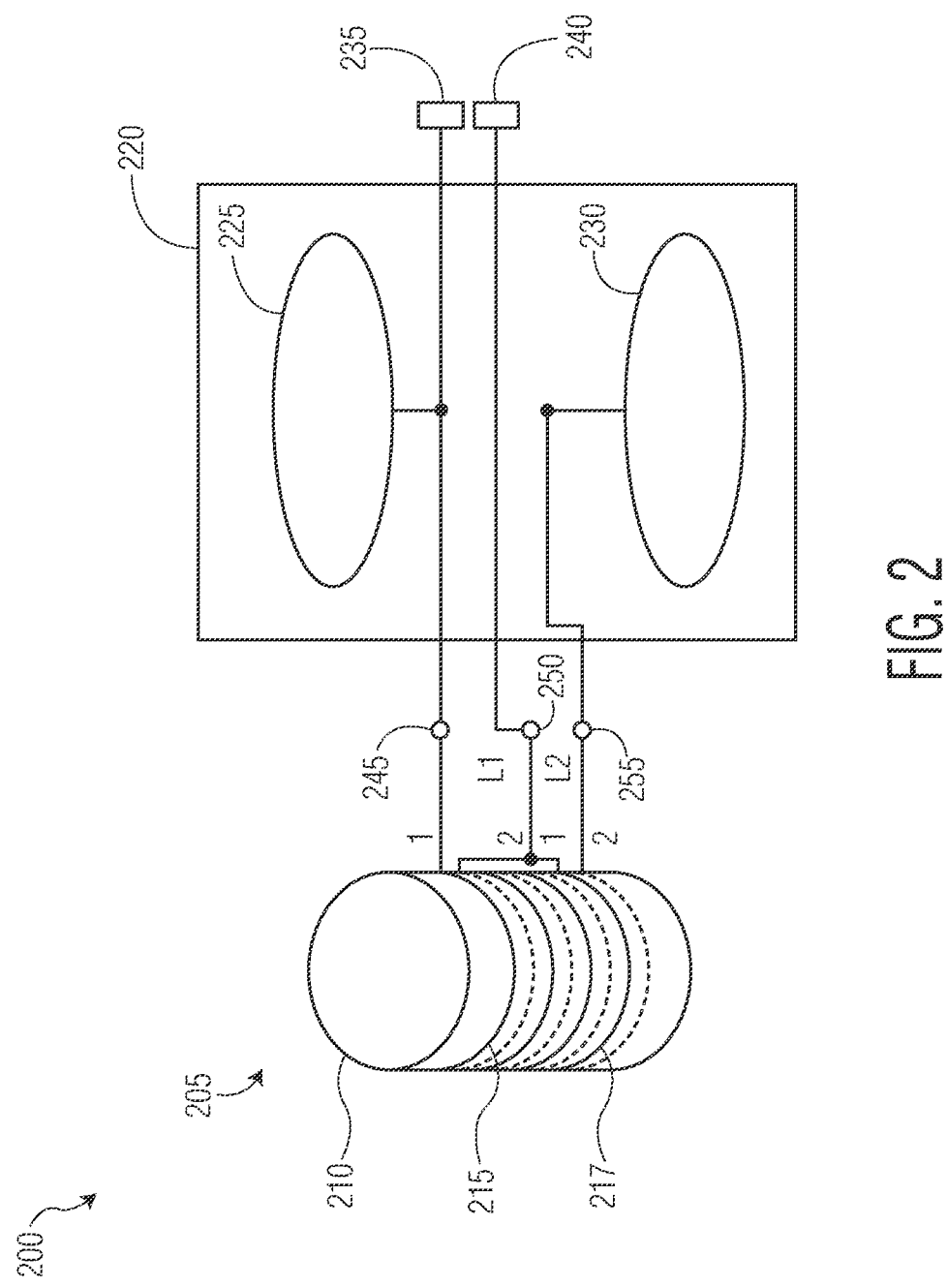
FIG. 2 is an example near-field antenna.

FIG. 2 is a first example near-field antenna 200. The antenna 200 includes a short loaded dipole portion 220 with two conductive loading plates 225, 230 and a small loop antenna 205.

The small loop antenna includes at least two coupled coils 215 and 217. The first coil 215 has an inductance of L1, and the second coil 217 has an inductance of L2. Both coils 215 and 217 may be connected, at connection point 250, such that they form a larger inductance compared with the inductance of the first coil 215 and the second coil 217.

Both coils 215 and 217 may be air coils, or wrapped around a ferrite core 210 as shown, or they can be in the form of a planar structure.

In the ferrite core 210 version, the coils 215 and 217 may be wrapped around the core 210 in an interleaved fashion, or wrapped on top of one another, i.e., the second coil 217 is first wrapped around the core 210, and then the first coil 215 is then wrapped around the core 210 on top of the second coil 217.

Connection point 245 couples one end of the first coil 215 to a first feeding connection 235 and to the first plate of the small loaded dipole 225. Connection point 250 couples another end of the first coil 215 to one end of the second coil 217 and to a second feeding connection 240. Connection point 255 couples another end of the second coil 217 to the second plate 230 of the small loaded dipole 220. The first and second feeding connections 235, 240 are coupled to the tuning circuit 104.

Figure 3C:
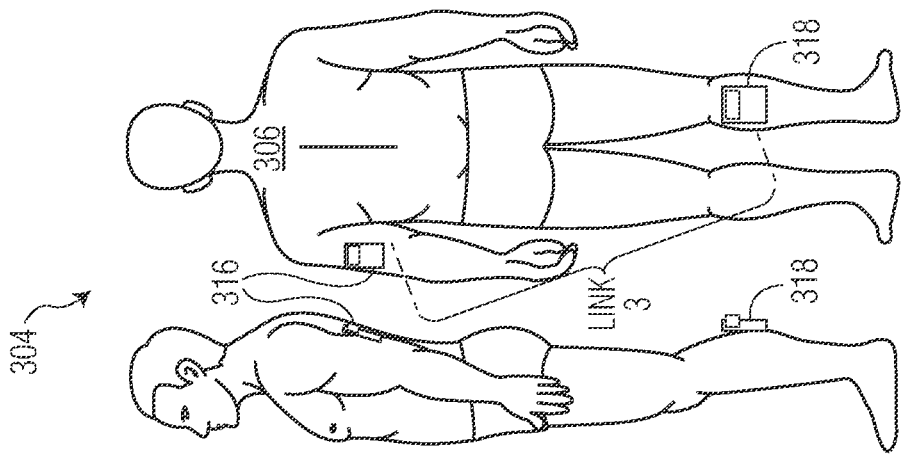
FIGS. 3A, 3B and 3C are example pictorial positionings of a pair of the near-field devices.
Figure 3B:
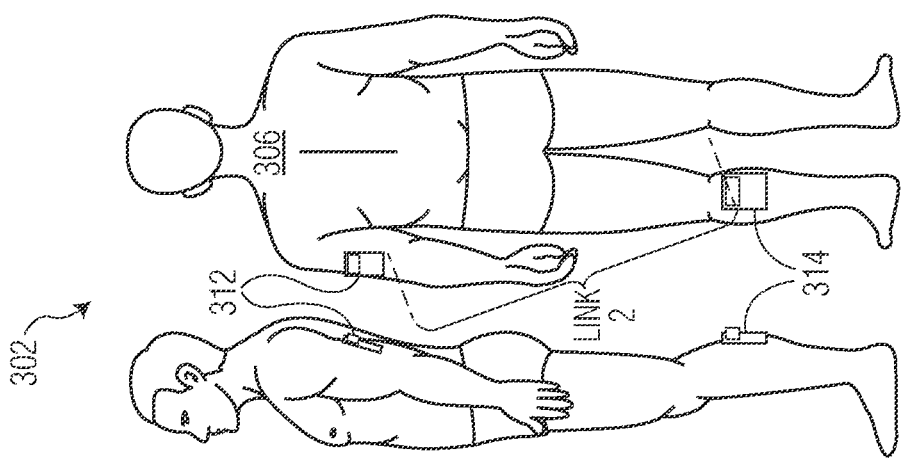
Figure 3A:
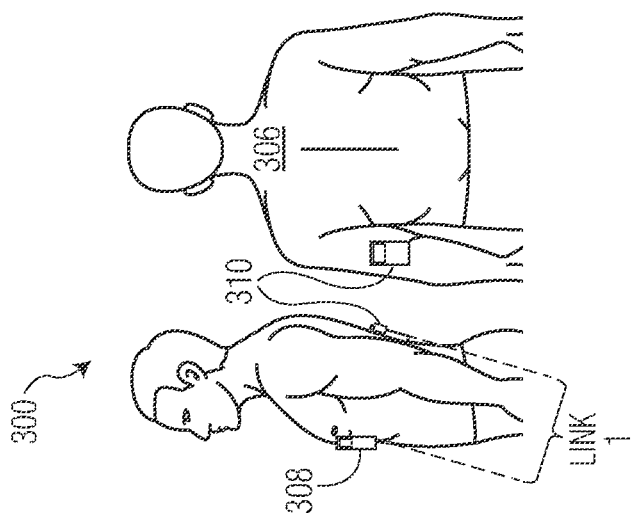

FIGS. 3A, 3B and 3C are example pictorial positionings 300, 302, 304 of a pair of the near-field devices, where at least one or more includes the near-field positioning device 100.

Example 300 shows a user 306 having a first near-field device 308 positioned at a central chest location and a second near-field device 310 positioned at a back side of a left upper arm. This configuration creates a first near-field communications link (e.g. link 1), corresponding to a first on-body channel model. Empirical data for the channel model can be captured by way of the received signal strength (RSS) at a receiving near-field device (e.g. 310) for a given transmitter voltage at a transmitting near-field device (e.g. 308).

Example 302 shows the user 306 having the first near-field device 312 positioned at a back side of a left upper arm and the second near-field device 314 positioned at the back side of a left lower leg. This configuration creates a second near-field communications link (e.g. link 2), corresponding to a second on-body channel model.

Example 304 shows the user 306 having the first near-field device 316 positioned at the back side of the left upper arm and the second near-field device 318 positioned at a back side of a right lower leg. This configuration creates a third near-field communications link (e.g. link 3), corresponding to a third on-body channel model.

Other near-field device positions are also possible including at: wrists, abdomen, lower arm, upper leg, as well as many more. The near-field devices can be on a same side of the body (e.g. link from a left wrist to a left leg) and on opposite sides of the body (e.g. a link from a left wrist to a right leg).

The device controller 108 in the devices 100 is configured to store and/or receive a set of on-body channel models for a predefined number of modeled communications link pairs (e.g. link 1, link 2, link 3, and possibly many more) corresponding to a predefined number of near-field wireless device position pairs.

In the discussion that follows, a set of near-field communications links were created based on a set of device positions and a set of body-parameters and a set of empirical RSS (received signal strength) readings taken. Users hosting the wireless devices were spread in age, gender, body height and weight. Measured results reported here were performed using two types of antennas (e.g. a planar design for body surface mount, and a wristband design). These measurements show how one or more on-body channel parameters varies based on both the wireless device positions and user body-parameters. Findings indicated that certain device positions were less suited for robust near-field wireless communications than others. A set of near-field on-body channel models were then derived that predicted these measurements.

Figure 4:
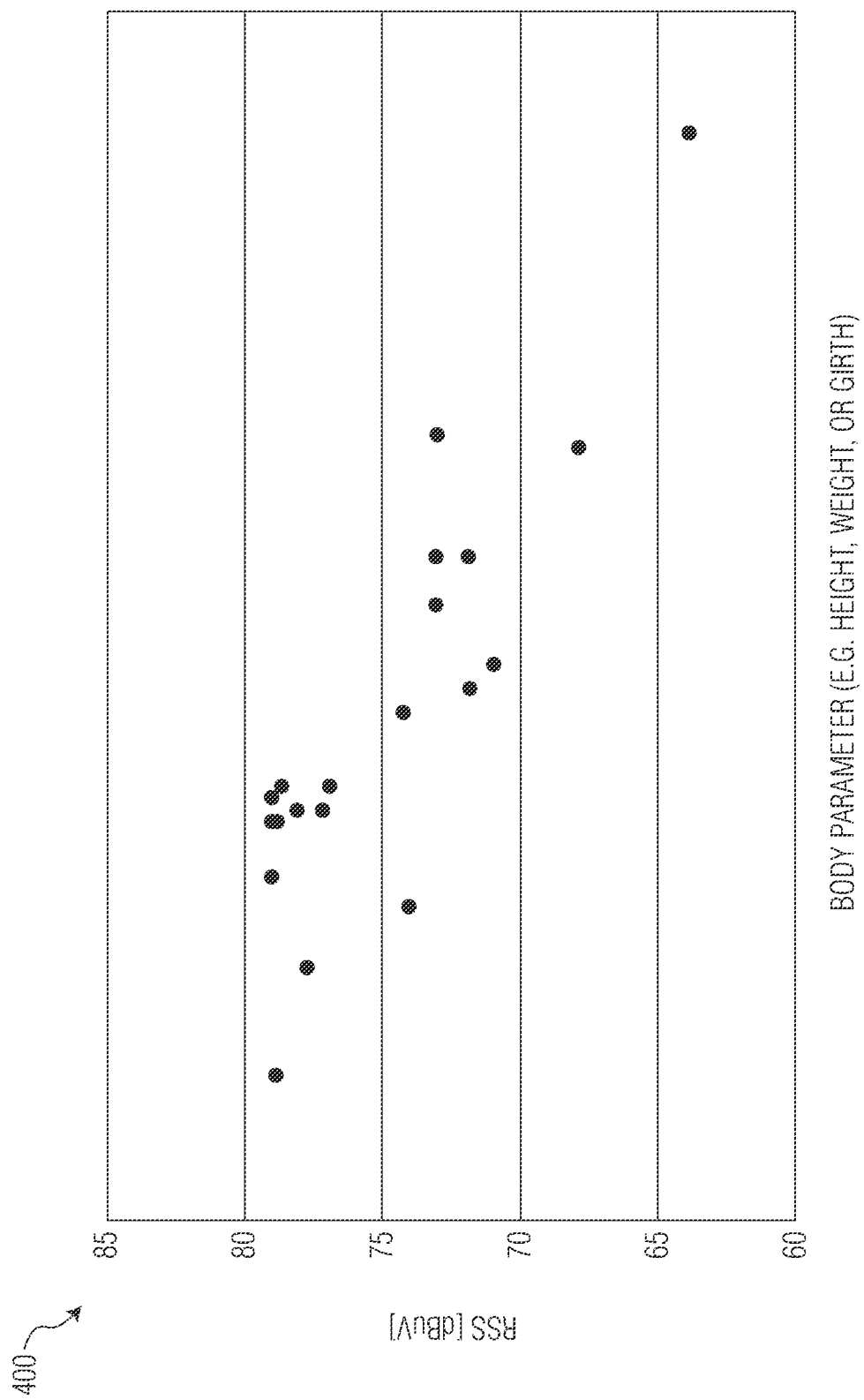
FIG. 4 shows an example graph of empirical RSS (Received Signal Strength) [dBuV] data measured as a set of body-parameter (e.g. a user's height, weight, or girth) varied.

FIG. 4 shows an example graph 400 of empirical RSS (Received Signal Strength) [dBuV] data measured as a body-parameter (e.g. a user's height, weight, or girth) varied. In this example 400 the empirical RSS is negatively correlated with a user's height, weight, or girth, with RSS decreasing as either the height, weight, or girth increased.

The received signal strength (RSS) measured on each test person when he/she is standing stationary is depicted versus each of his/her body-parameters: body height, body weight and body girth (e.g. waist circumference).

For the device positions shown in Table 1 below, the empirical RSS data showed a significant correlation with respect to one or more body-parameters (i.e. the empirical data had a high Pearson correlation coefficient and the p-value indicated statistical significance).

TABLE 1

Link 1-Left wrist and right lower leg
Link 2-Left wrist and left upper arm
Link 3-Left abdomen and right abdomen A near-field on-body channel model was then created for these Links (1, 2, 3) in analogy with radio wave propagation and a free space path loss equation, as follows. In free space a relation between the transmit and receive power is given by the Friis free space equation Eq. 1, $$P_R = P_T + G_T + G_R + 10\log\left(\frac{\lambda^2}{(4\pi)^2 d^2}\right) \quad \text{Eq. 1}$$

$P_T$ and $P_R$ are the transmitted and received powers in dBm, $G_T$ and $G_R$ are the transmitter and receiver gains in dB, $\lambda$ is the wavelength and d is the distance between transmitter and receiver in meters. As follows an RF link budget in free space can be written as, $$RF \text{ Link budget [dB]} = P_R - P_T = G_T + G_R + 10\log\left(\frac{\lambda^2}{(4\pi)^2 d^2}\right) \quad \text{Eq. 2}$$

A more general an RF link budget can be written as, $$RF \text{ Link budget [dB]} = \quad \text{Eq. 3}$$
$$P_R - P_T = G_T + G_R + 20\log\left(\frac{\lambda}{4\pi}\right) + 10n \log\left(\frac{1}{d}\right)$$

Where n denotes the path loss exponent and n=2 in case of free space. In addition, n was found by measurement to range from 3 to 5 for indoor links depending on the building's specifics. Following Eq. 3 an RF link budget for a fixed RF operating frequency can be written as, $$RF \text{ Link budget[dB]} = 10n\log\left(\frac{1}{d}\right) + \{G_T + G_R + C\} \quad \text{Eq. 4}$$

Where $G_T$ and $G_R$ are the transmitter and receiver gains in dB at the selected RF operating frequency and C is a constant value for the selected RF operating frequency.

Therefore all values grouped at the right side between { ... } are constants for the selected RF operating frequency. In case of the Near-field measured data, the received signal strength $V_{RX}$ [dBuV] is measured for a fixed transmitter power $V_{TX}$ of 132 dBuV, both at the selected Near-field operating frequency. Then, $$\text{Near Field Link budget [dB]} = V_{RX} - V_{TX} \qquad \text{Eq. 5}$$

And when deriving an Near-field link budget formula in analogy to Eq. 4, $$\text{Near Field Link budget [dB]} = 10\, a \log\left(bp_0 \frac{1}{BP}\right) + b \qquad \text{Eq. 6}$$

Where body-parameter BP (i.e. body height, body weight or front body circumference) is normalized in dimension by means of $bp_0$ (i.e. 1 cm, 1 kg or 1 cm) and coefficients a and b are the model's curve fitting coefficients. Note that the coefficient "a" is defined in analogy with the path loss exponent "n" in Eq. 4, thus "a" is a path loss exponent between a pair of devices in the set of near-field wireless devices.

FIG. 5 shows an example 500 table of near-field on-body channel models created for Links (1, 2, 3). The models were created based on the empirical data measured with the near-field devices in FIG. 2 for Links 1, 2 and 3 in Table 1.

In some example embodiments, the near-field positioning device 100 can be configured to send its specific user's RSS data, the selected positions and the set of body-parameters back to a near-field device manufacture such that the manufacture can add to the set of training data and update the "a" and "b" curve fitting constants in the near-field channel loss model which then can be transmitted back to a large number of near-field devices 100 for many different users.

Figure 6A:
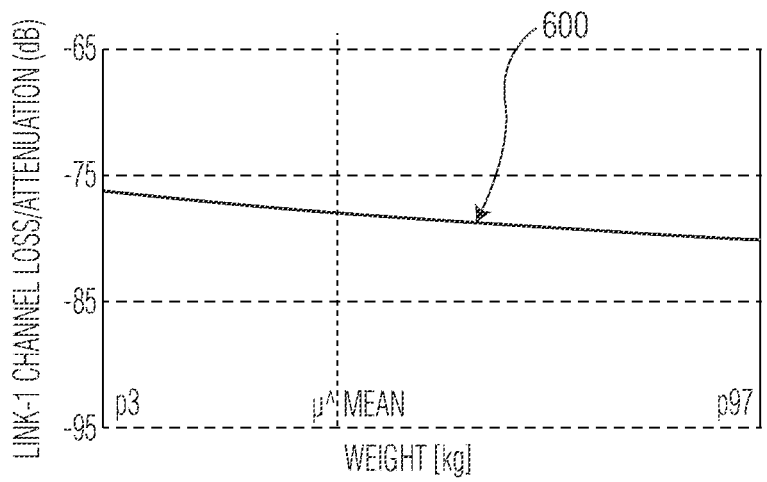
FIGS. 6A, 6B, 6C shows example graphs of calculated near-field channel loss model for Links (1, 2, 3).
Figure 6B:
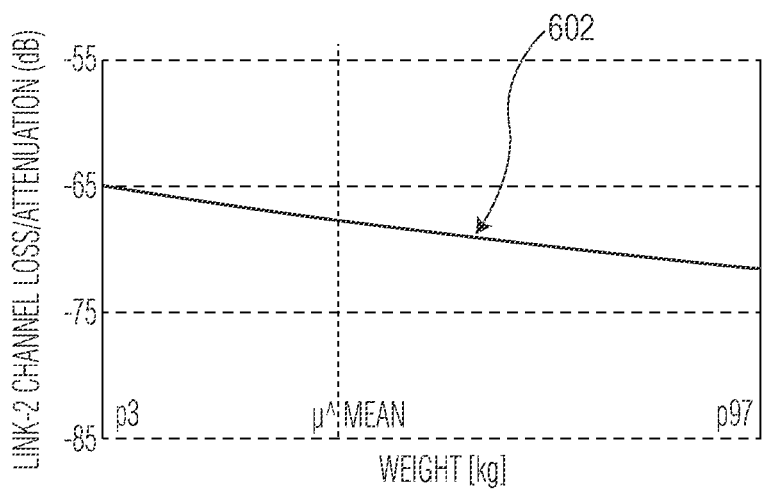
Figure 6C:
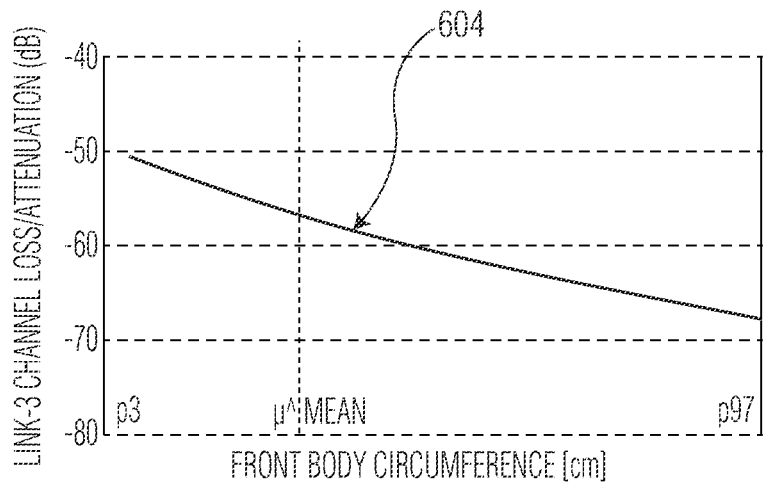

FIGS. 6A, 6B, 6C shows example graphs of calculated near-field channel loss model for Links (1, 2, 3). Each graphs x-axis is a body-parameter (e.g. weight, girth (i.e. front body circumference)) increasing from left to right, and y-axis is the calculated near-field channel loss based on Eq. 6 and a set of user training data to set variables "a" and "b".

An average/mean body-parameter value "μ" is identified, bounded by a p3 and a p97 percentile of the body-parameter based on available statistics for the body parameters in case of the Belgian population, to which the test persons belong.

Indicator p3 means that for 3% of the Belgian population the body parameter will be inferior to the p3-value specified. Indicator p97 means that for 97% of the Belgian population the body parameter will not exceed the p97-value specified. Both indicator p3 and p97 are depicted in the graphs to demonstrate that the set of user training data is between these two indicators and hence, the set of user training data covers well the majority of the Belgian population with respect to the body parameters.

FIG. 6A shows an example calculated near-field channel loss model 600 for Link-1 (i.e. Left wrist and right lower leg) calculated based on the user's weight using Eq. 6. A mean μ loss/attenuation for Link-1 from the set of user training data is about −78 dB.

FIG. 6B shows an example calculated near-field channel loss model 602 for Link-2 (i.e. Left wrist and left upper arm) calculated based on the user's weight using Eq. 6. A mean μ loss/attenuation for Link-2 from the set of user training data is about −67 dB.

FIG. 6C shows an example calculated near-field channel loss model 604 for Link-3 (i.e. Left abdomen and right abdomen) calculated based on the user's girth (e.g. front body circumference) using Eq. 6. A mean μ loss/attenuation for Link-3 from the set of user training data is about −57 dB.

If an example user's body-parameters corresponded to the mean μ values, then the channel loss model calculations based on such body-parameters indicates that Link-3 has the least loss (i.e. attenuation). In response the near-field positioning device 100 would recommend Link-3 first as a best position for a pair of other near-field devices.

Measured deviations in dB between Eq. 6 model and actual measured RSS link budget values is shown in Table 3 and are relatively small, thus validating the calculated near-field channel loss model curves 600, 602, 604.

TABLE 3

| | |
|---|---|
| Link 1-Left wrist and right lower leg | 0.5 dB |
| Link 2-Left wrist and left upper arm | 0.5 dB |
| Link 3-Left abdomen and right abdomen | 1.5 dB |

Applications of the Invention

An artificial pancreas system is one application/use-case. Such a system could consist of a glucose sensor in a first near-field wireless device and an insulin pump in a second near-field wireless device (that includes the near-field positioning device 100). The sensor monitors the blood glucose level and communicates this to the pump via a near-field link which then injects a necessary amount of insulin, thereby forming an autonomous closed loop system.

A method to position the wireless devices on-body can be as follows: At start-up of this system the patient will need to attach the sensor and the pump to his body. Channel models for a set of device positions were derived with the actual sensor and pump products in advance at the manufacturer's side and stored in, for example, the insulin pump. These channel models can then be used to select the optimal position for the glucose sensor and for the insulin pump by comparing the Eq. 6 calculated channel loss model values for each of the device positions based on the patient's body-parameters (e.g. body height, body weight and front body circumference).

In an alternate method, a first near-field device (that includes the near-field positioning device 100) has a fixed position defined perhaps by the near-field device manufacturer; however, a second near-field device can have a number of possible positions. If a user places the second device at position A or B, then using the Eq. 6 channel loss model, a controller in the first device can infer whether the second device is located at position A or B by comparing the measured RSS to the calculated RSS at A and B.

Other applications include wearables for wireless on-body networks that require a small form factor.

Various instructions and/or operational steps discussed in the above Figures can be executed in any order, unless a specific order is explicitly stated. Also, those skilled in the art will recognize that while some example sets of instructions/steps have been discussed, the material in this specification can be combined in a variety of ways to yield other examples as well, and are to be understood within a context provided by this detailed description.

In some example embodiments these instructions/steps are implemented as functional and software instructions. In other embodiments, the instructions can be implemented either using logic gates, application specific chips, firmware, as well as other hardware forms.

When the instructions are embodied as a set of executable instructions in a non-transitory computer-readable or computer-usable media which are effected on a computer or machine programmed with and controlled by said executable instructions. Said instructions are loaded for execution on a processor (such as one or more CPUs). Said processor includes microprocessors, microcontrollers, processor modules or subsystems (including one or more microprocessors or microcontrollers), or other control or computing devices. A processor can refer to a single component or to plural components. Said computer-readable or computer-usable storage medium or media is (are) considered to be part of an article (or article of manufacture). An article or article of manufacture can refer to any manufactured single component or multiple components. The non-transitory machine or computer-usable media or mediums as defined herein excludes signals, but such media or mediums may be capable of receiving and processing information from signals and/or other transitory mediums.

It will be readily understood that the components of the embodiments as generally described herein and illustrated in the appended figures could be arranged and designed in a wide variety of different configurations. Thus, the detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

What is claimed is:

1. A near-field positioning device, comprising:
an input interface configured to receive a set of body-parameters from a user;
a controller configured to generate a set of recommended positions for a set of near-field wireless devices to be coupled to the user based on the body-parameters; and
an output interface configured to output the set of recommended positions;
wherein the controller is configured to receive from the input interface a fixed position for a first one of the set of near-field wireless devices; and
wherein the controller is configured to select a recommended position for a second one of the set of near-field wireless devices from the set of recommended positions that have a near-field channel loss less than a maximum channel loss.

2. The device of claim 1:
wherein the set of recommended positions is based on an on-body near-field channel loss model.

3. The device of claim 2:
wherein the near-field channel loss model is configured to predict a near-field channel loss over a range of user body-parameters.

4. The device of claim 2:
wherein the controller is configured to divide the set of near-field wireless devices into a set of device pairs, and define each device pair as a separate communications link; and
wherein a separate near-field channel loss model is calculated for each separate communications link based on the set of body-parameters.

5. The device of claim 1:
wherein the controller is configured to predict a near-field channel loss for each of the set of wireless devices located at the set of recommended positions on the user.

6. The device of claim 1:
wherein the controller is configured to include in the set of recommended positions those wireless devices in the set of near-field wireless devices that have a near-field channel loss less than a maximum channel loss.

7. The device of claim 1:
wherein the controller is configured to rank the set of recommended positions of the set of near-field wireless devices from a lowest near-field channel loss to a highest near-field channel loss.

8. The device of claim 2:
wherein the near-field channel loss model includes, $$\text{Near Field Link budget [dB]} = 10\, a \log\left(bp_0 \frac{1}{BP}\right) + b$$

wherein BP is a body-parameter from the set of body-parameters;
wherein $bp_0$ normalizes BP to a unitless quantity; and
wherein coefficients "a" and "b" are curve fitting coefficients.

9. The device of claim 8:
wherein "a" is a path loss exponent between a pair of devices in the set of near-field wireless devices.

10. The device of claim 2:
wherein the controller is configured to receive from the input interface an RSS (received signal strength) signal corresponding to a pair of wireless device positions;

wherein the controller is configured to transmit the RSS, the selected positions and the set of body-parameters from the output interface to a near-field channel loss model training site; and wherein the training site is configured to add the RSS, the selected positions and the set of body-parameters to a set of training data used to update the near-field channel loss model.

11. The device of claim 1:

wherein the body-parameters include at least one of a body: topology, weight, height, girth, or position.

12. The device of claim 1:

wherein the controller is configured to substitute a mean body-parameter if a corresponding body-parameter is not received from the user.

13. The device of claim 12:

wherein the mean body-parameter is an average value of the corresponding body-parameter based on a set of training data collected from a set of users.

14. The device of claim 1:

wherein the user is at least one of: a robot, a vehicle, a docking system, a physical coupling system, a ticketing station, a security portal, an assembly line device, a human body, an animal body, a body of a living organism, or a body structure of an inanimate object.

15. The device of claim 1:

wherein the near-field device is embedded in at least one of: a vehicle, a game controller, an amusement park ride, a medical device, an industrial station, or a robotic device.

16. A near-field positioning device, comprising:

an input interface configured to receive a set of body-parameters from a user;

a controller configured to generate a set of recommended positions for a set of near-field wireless devices to be coupled to the user based on the body-parameters; and an output interface configured to output the recommended positions;

wherein the near-field positioning device is embedded in a near-field wireless device from the set of near-field wireless devices;

wherein the near-field wireless device includes a front-end portion configured to translate signals from the controller into near-field signals exchanged with a second near-field device; and wherein the front-end portion includes,
 a near-field antenna having a first conductive surface and a second conductive surface;
 wherein the conductive surfaces are configured to carry non-propagating quasi-static near-field electric-induction (NFEI) signals exchanged within the near-field communications link; and
 a tuning circuit coupled to the near-field antenna and having a set of tuning parameters and configured to adjust a resonant frequency and bandwidth of the near-field antenna.

17. A near-field positioning device, comprising:

an input interface configured to receive a set of body-parameters from a user;

a controller configured to generate a set of recommended positions for a set of near-field wireless devices to be coupled to the user based on the body-parameters; and an output interface configured to output the recommended positions;

wherein the near-field positioning device is embedded in a near-field wireless device from the set of near-field wireless devices;

wherein the near-field wireless device includes a front-end portion configured to translate signals from the controller into near-field signals exchanged with a second near-field device; and wherein the front-end portion includes,
 a near-field antenna having a coil;
 wherein the coil is configured to carry non-propagating quasi-static near-field magnetic-induction (NFMI) signals exchanged within the near-field communications link; and
 a tuning circuit coupled to the near-field antenna and having a set of tuning parameters and configured to adjust a resonant frequency and bandwidth of the near-field antenna.

* * * * *